United States Patent [19]

Rice et al.

[11] Patent Number: 4,775,759

[45] Date of Patent: Oct. 4, 1988

[54] SYNTHESIS AND UTILIZATION OF 17-METHYL AND 17-CYCLOPROPYLMETHYL-3,14-DIHYDROXY-4,5α-EPOXY 6β-FLUOROMORPHINANS (FOXY AND CYCLOFOXY) AS (18F)-LABELED OPIOID LIGANDS FOR POSITION EMISSION TRANSAXIAL TOMOGRAPHY (PETT)

[75] Inventors: Kenner C. Rice, Rockville; Candace B. Pert, Bethesda; Terrence R. Burke, Jr., West Bethesda; Steven M. Larson, Cabin John; William C. Eckelman, Rockville; Michael A. Channing, Annapolis, all of Md.

[73] Assignee: The United States of America as represented by the Department of Health and Human Services, Washington, D.C.

[21] Appl. No.: 675,276

[22] Filed: Nov. 27, 1984

[51] Int. Cl.$^4$ .................... A61K 43/00; A61K 49/02; C07D 489/08
[52] U.S. Cl. ...................... 546/44; 424/1.1; 424/9
[58] Field of Search ....................... 546/44

[56] References Cited

U.S. PATENT DOCUMENTS

| 3,137,701 | 6/1964 | Ayer | 546/46 |
| 3,254,088 | 5/1966 | Lowenstein et al. | 546/45 |
| 3,332,950 | 7/1967 | Blumberg et al. | 546/44 |
| 4,241,065 | 12/1980 | Boswell, Jr. et al. | 546/46 X |
| 4,451,470 | 5/1984 | Ganti | 546/44 |

OTHER PUBLICATIONS

Phelps et al. "Positron Computed Tomography for Studies of Myocardial and Cerebral Function," *Annals of Internal Medicine,* 98:339–359, 1983.
Burke, et al., "Probes for Narcotic Receptor Mediated Phenomena 8. Tritiation of Irreversible mu or delta Specific Opioid Receptor Affinity Ligands to High Specific Activity," *Journal of Labelled Compounds and Radiopharmaceuticals,* 21(8):693–702, 1984.
Pert et al., "[$^{18}$F]-3-Acetylcyclofoxy: A Useful Probe for the Visualization of Opiate Receptors in Living Animals, *FEBS Lett.,* vol. 177, No. 2, pp. 281–286 (11/19/84).
Goodman, et al., The Pharmacological Basis of Therapeutics, 7th ed., MacMillan Pub. Co., New York, pp. 491–531.
The Merck Index, 10th ed., Merck & Co., Rahway, N.J., p. 912 (1983).
Chemical Abstracts Index Guide (1985), pp. 341g and 1048g.
Bognar, et al., Chemical Abstracts, vol. 77, 19840k (1972).
Malkleit, et al., Chemical Abstracts, vol. 77, 152405p (1972).
Makleit, et al., Chemical Abstracts, vol. 85, 177742z (1976).
Somogyi, et al., Chemical Abstracts, vol. 87, 16824Oy (1977).
Somogyi, et al., Chemical Abstracts, vol. 90, 23347r (1979).
Rothman, et al., Neuropeptides(Edinburgh) vol. 4, No. 4, pp. 311–317 (1984).
Rothman, et al., Chemical Abstracts, vol. 101, 166627p (11/05/84).
Pert, et al., (FEBS Letters, vol., 177, No. 2, pp. 281–286 (11/19/84).

*Primary Examiner*—Donald G. Daus
*Assistant Examiner*—Diana G. Rivers

[57] ABSTRACT

Fluorinated derivatives 3,14-dihydroxy-4,5α-epoxy-6β-fluoro-17-methylmorphinan ("fluorooxymorphone"; FOXY, compound 10) and 17-cyclopropylmethyl-3,14-dihydroxy-4,5α-epoxy-6β-fluoromorphinan (CYCLOFOXY, compound 18) are prepared based upon the structures of the potent opioid agonist oxymorphone 4 and the antagonist naltrexone 11, respectively. Fluorine was introduced in the final stages of synthesis by a facile nucleophilic displacement with fluoride ion of the 6α-triflate functions in 8 and 16. The synthetic procedures were suitable for the production of the corresponding positron emitting $^{18}$F-labeled analogs $^{18}$F-FOXY and $^{18}$F-CYCLOFOXY, which are useful for in vivo studies of the opioid receptor system using positron emission transaxial tomography. In addition, the tritiation of FOXY (10) to high specific activity is noted.

4 Claims, No Drawings

SYNTHESIS AND UTILIZATION OF 17-METHYL AND 17-CYCLOPROPYLMETHYL-3,14-DIHYDROXY-4,5α-EPOXY 6β-FLUOROMORPHINANS (FOXY AND CYCLOFOXY) AS (18F)-LABELED OPIOID LIGANDS FOR POSITION EMISSION TRANSAXIAL TOMOGRAPHY (PETT)

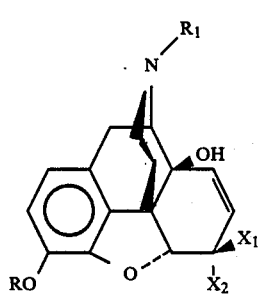

FORMULA I-A

| | R | $R_1$ | $X_1$ | $X_2$ |
|---|---|---|---|---|
| 1 | Me | Me | | =O |
| 2 | Me | Me | H | OH |

FORMULA I-B

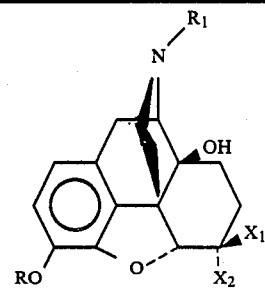

| | R | $R_1$ | $X_1$ | $X_2$ |
|---|---|---|---|---|
| 3 | Me | Me | H | OH |
| 4 | H | Me | | =O |
| 5 | H | Me | H | OH |
| 6 | H | Me | OH | H |
| 7 | Ac | Me | H | OH |
| *8 | Ac | Me | H | OTf |
| *9 | Ac | Me | F | H |
| *10 | H | Me | F | H |
| 11 | H | CPM | | =O |
| 12 | H | CPM | H | OH |
| 13 | H | CPM | OH | H |
| 14 | Ac | CPM | H | OH |
| 15 | Ac | CPM | OH | H |
| *16 | Ac | CPM | H | OTf |
| *17 | Ac | CPM | F | H |
| *18 | H | CPM | F | H |

FORMULA I-C

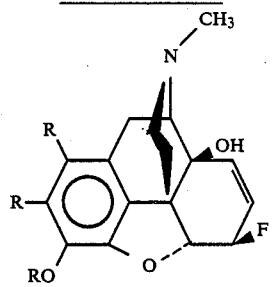

| *19 | R = Br |
| *20 | R = ³H |

OTf = Trifluoro methane sulfonyl
CPM = Cyclopropylmethyl
Compound 10, FOXY
Compound 12, 6-α-naltrexol
Compound 18, CYCLOFOXY
* = New compound

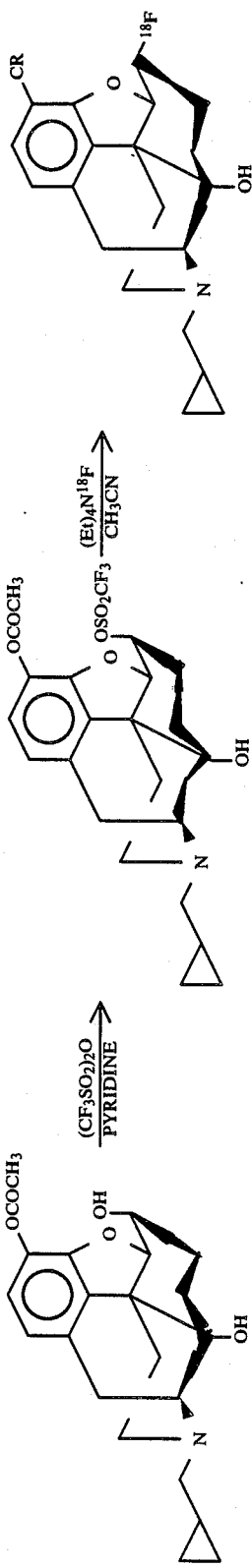
SYNTHESIS OF [¹⁸F]—3-ACETYLCYCLOFOXY (17)
14: 3-ACETYL-6α-NALTREXOL
16: 3-ACETYL-6α-NALTREXOL TRIFLATE
17: R = CH₃CO, 3-ACETYL-6-DEOXY-6β-FLUORONALTREXONE (3-ACETYLCYCLOFOXY)
18: R = H, 6-DEOXY-6β-FLUORONALTREXONE (CYCLOFOXY)
10: 6-DEOXY-6β-FLUOROOXYMORPHONE (FOXY)
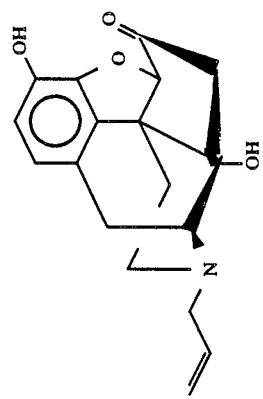
(−)-NALOXONE
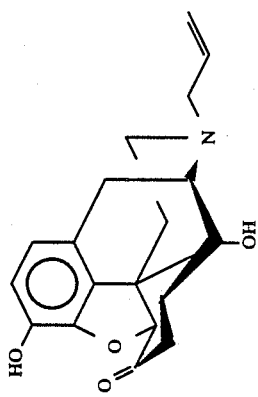
(+)-NALOXONE The structure and function of the opioid receptor system is set out in the synthesis of a variety of opioid ligands designed as pharmacological probes of the system. One shortcoming of these lines of investigation is that they are not suitable for in vivo visualization of opioid receptors in the living human brain. With the development of positron emission transaxial tomography (PETT), in vivo investigation of the opioid receptor system in humans is possible if an appropriate positron emitting opioid ligand is used (see Phelps et al, *Annals of Internal Medicine,* 98:339–359, 1983). To be useful, such a ligand must have high binding affinity and specificity for the opioid receptor system and must be synthetically accessible by introduction of the positron emitting isotope in rapid, high yield reaction immediately prior to use. Use of $^{18}F$, a positron emitting isotope with a half life of 110 min, has proven to be successful for PETT scanning in other systems. PETT as here used is a non-invasive method for counting or scanning opiate receptors. Described herein is the synthesis of four new fluorinated opioids 9, 10, 17 and 18 by routes which involve facile introduction of fluorine in the final stages in a manner suitable for incorporation of $^{18}F$. Synthesis of the $^{18}F$-labeled 17 (a prodrug of Cyclofoxy 18) and utilization of this material for visualization of opiate receptors in the brain of a living baboon is also included. Also included in this invention is the tritiation of 10 to high specific activity.

PROCESS OF PREPARATION

Morphinan 10 ("fluorooxymorphone," FOXY), whose structure is based on the potent opioid agonist oxymorphone (4), was obtained in a clean, rapid (20 min) reaction of triflate 8 with KF/18-crown-6 in refluxing acetonitrile. The choice of triflate (trifluoromethanesulfonate) as the leaving group in this nucleophilic displacement is based upon its proven value in similar reactions and the observation that methyl triflates are $10^{4.3}$ times more reactive to solvolysis than tosylates. In the reaction of 8 with fluoride the 3-OAc group was retained, giving 9, which upon treatment with aqueous $NH_3$ yielded the title compound FOXY (10). However, for experiments utilizing $^{18}F$ where shorter reaction times are critical, the 3-OAc derivative 9 can be taken directly for in vivo studies, eliminating the hydrolysis step. By analogy to other 3-OAc 4,5-epoxymorphinans such as heroin, the presence of the 3-OAc group in 9' and 17' is believed to facilitate uptake in the brain where rapid enzymatic deacetylation yields the free [$^{18}F$]3,14-dihydroxy-4,5α-epoxy-6β-fluoro-17-methylmorphinan, or $^{18}F$-FOXY (10') and [$^{18}F$]17-cyclopropylmethyl-3,14-dihydroxy-4,5α-epoxy-6β-fluoromorphinan, or $^{18}F$-CYCLOFOXY (18').

Triflate 8 was prepared by reaction of 6 —OH compound 7 with a molar excess of trifluoromethanesulfonic anhydride in pyridine/$CHC_{13}$. The excess anhydride did not acylate the 14-OH group under these conditions. The 3-acetyl-14-hydroxy-dihydromorphine 7 was obtained as a crystalline solid, mp 125°–126° C. (previously reported as a gum) by treatment of the corresponding 3-OH compund 5 with acetic anhydride in aqueous $NaHCO_3$. The 3-OH compound 5 can be obtained directly from 14-hydroxydihydromorphinone (4) by reduction with $NaBH_4$. However, in contrast to previous reports, substantial formation of epimeric 6β-OH product 6 was observed, necessitating tedious purification by silica gel chromatography to obtain the pure 6 —OH epimer 5. Alternately, pure 6β-OH compound 2 was obtained by $NaBH_4$ reduction of the didehydro compound 1 which followed by hydrogenation to 3 and O-demethylation ($BBr_3$ in $CHCl_3$) yield 5.

PROPERTIES OF FOXY AND CYCLOFOXY

FOXY (10) has been shown to have a high affinity for opioid mu-receptors and exhibits one of the lowest levels of nonspecific binding for any mu-opioid ligand presently available. However, it has previously been reported that even agonists with very high in vivo receptor affinities accumulate poorly at receptor sites. Although two exceptions have been claimed, the usual failure to detect binding of opioid agonists in vivo may be due in part to their reduced affinity in the sodium-rich cellular environment. Antagonists, in contrast, have been shown to provide much better ligands for in vivo binding studies. In the epoxymorphinan series, N-cyclopropylmethyl compounds are generally narcotic antagonists. Therefore, the corresponding N-cyclopropylmethyl derivative (CYCLOFOXY, 18) as a ligand is probably superior to FOXY for in vivo receptor imaging.

SPECIFIC PREPARATION

Using a reaction sequence analogous to that described above for the synthesis of FOXY, the potent, prototype narcotic antagonist naltrexone (11) was reduced with $NaBH_4$ in THF to yield predominantly the 6α-OH epimer 12. (The observed NMR coupling constants for 12 were $J_{5\beta\text{-}6\beta}=4.4$ Hz.) A small amount of epimeric 13 also formed, which could be removed chromatographically at this point, or preferably carried to the next step where acetylation of the crude mixture with acetic anhydride in aqueous $NaHCO_3$ gave a more easily separable mixture of 3-OAc-6α-OH compounds 14 and 15, respectively.

Reaction of pure 14 with excess trifluoromethanesulfonic anhydride in pyridine/$CHCl_3$ gave the 6 OTf 16. As in the synthesis of FOXY, facile nucleophilic displacement of the triflate group with KF/18-crown-6 in refluxing acetonitrile gave the 3-OAc compound 17, which provided CYCLOFOXY (18) upon heating with aqueous $NH_3$ in MeOH. Vicinal NMR coupling constants between the 5β-H and 6-F of FOXY (J=18 Hz) and CYCLOFOXY (J=21 Hz) were consistent with the 6β-F configuration. [$^{18}F$]-3-Acetyl-6-deoxy-6-β-fluoronaltrexone ([$^{18}F$]-3-acetylcyclofoxy (17)) was synthesized from 14 via the triflate 16. $^{18}F$ was produced from $^{6}Li_2CO_3$ using the high flux reactor ($1.1\times 10^{14}n/cm^2/s$) at the National Bureau of Standards. The reaction of triflate 16 with [$^{18}F$]$Et_4NF$ in anhydrous acetonitrile containing $Et_4NOH$ at 80° C. for 0.25 h provided [$^{18}F$]-3-acetylcyclofoxy (17'). The product was purified on reversed phase HPLC eluted with 55% MeOH, 45% $H_2O$ with 0.5 mM octanesulfonic acid at pH 3 to give a 30% radiochemical yield uncorrected for decay. The lower limit of the effective specific activity at the time of injection was approximately 20 Ci/mmol assuming that all chemical impurities have the same extinction coefficient and the same opiate receptor affinity constant. By Scatchard analysis of [$^{18}F$]-3-acetylcyclofoxy (17') and [$^{3}H$]-(—)-naloxone binding to rat brain membranes the specific activity was estimated to be approxiamtely 50 Ci/mmol.

It is of interest to have both FOXY and CYCLOFOXY labeled with tritium in high specific activity for receptor binding and autoradiographic studies. In a procedure similar to that previously used to tritiate other opioid ligands, FOXY was brominated (Br$_2$ in AcOH) to yield the dibromo derivative 19. Palladium on carbon catalyzed exchange of tritium for bromine gave $^3$H-FOXY (20) with a specific activity of 16 Ci/mmol.

Animal studies utilizing PETT show the superior binding ability and $^{18}$F-3-acetylcyclofoxy accumulation in opiate receptor rich brain regions of both rat and baboon. This binding is shown to be completely displaced by the active enantiomer of naloxone [(−)-naloxone] while the identical dose of the pharmacologically inert (+)-naloxone has no detectable effect. Moreover, both rat and baboon brain showed the well documented, typical opiate receptor distribution so tht basal ganglia and thalamus are clearly visible in the living baboon brain up to 95 minutes after intravenous injection of [$^{18}$F]-3-acetylcyclofoxy. Acetylcyclofoxy operates as a prodrug in this case and shows that CYCLOFOXY is a highly specific opiate receptor ligand.

Studies were made with the baboon where CYCLOFOXY positron emitting species was localized in areas of the brain. Very strong evidence is shown that in fact this compound occupied opiate receptors with this drug derived from the observation that naloxone, which is used to revive narcotic overdose patients, completely displaced the radioactive counts that were observed from CYCLOFOXY. It was further observed that the unnatural isomer of naloxone, the pharmacologically inert form, had no effect on the radioactivity in the opiate receptor containing tissue. This was strong evidence for receptor occupancy. The PETT scan can be made quantitative. The receptor occupancy can be quantitated by the computer in the system as a function of the specifically bound labeled compound.

Relative especially to the use of the compounds of this invention as a probe of visualization of opiate receptors in living animals, it was observed that acetylcyclofoxy, which is a prodrug that is converted into CYCLOFOXY in the body by metabolic deacetylation, is a model for the behavior of these compounds. Compounds useful in the visualization include $^{18}$F-3-acetylcyclofoxy (the prodrug), $^{18}$F-cyclofoxy (the drug), and equivalent compounds derived from naloxone. The preparation of the CYCLOFOXY is by a one-step triflate displacement reaction where the triflate group is CF$_3$SO$_2$O and using a positron emitting $^{18}$F ion from tetraethylammonium $^{18}$F fluoride.

Relative to the tritiated compound 20, this compound has been found to be highly specific mu-opiate receptor ligand and the substitution in the molecule of the tritium ($^3$H) substituents renders these compounds valuable for autoradiographic visualization of opiate receptors.

As to naloxone, this compound, which has the N-allyl group, is utilized for its antagonist properties (see U.S. Pat. No. 3,254,088 Lewenstein et al) and the naltrexone containing the N-cyclopropylmethyl group is utilized also for antagonist properties (see U.S. Pat. No. 3,332,950 Blumberg). It is further noted that the FOXY compounds are narcotic agonists and the CYCLOFOXY compounds are antagonist to the narcotics.

MATERIAL INFORMATION DISCLOSURE

Phelps et al, "Positron Computed Tomography for Studies of Myocardial and Cerebral Function," *Annals of Internal Medicine*, 98:339–359, 1983.

Burke et al, "Probes for Narcotic Receptor Mediated Phenomena 11. Synthesis of 17-methyl and 17-cyclopropylmethyl-3,14-dihydroxy-4,5α-epoxy-6β-fluoromorphinans (Foxy and Cyclofoxy) as Models of Opioid Ligands Suitable for Positron Emission Transaxial Tomography," submitted to *Heterocycles*, 1984.

Burke, et al, "Probes for Narcotic Receptor Mediated Phenomena 8. Tritiation of Irreversible mu or delta Specific Opioid Receptor Affinity Ligands to High Specific Activity," *Journal of Labelled Compounds and Radiopharmaceuticals*, 21(8):693–702, 1984.

Pert, et al, "[$^{18}$F]-3-Acetylcyclofoxy: A Useful Probe for the Visualization of Opiate Receptors in Living Animals, *FEBS Lett.*, in press, 1984.

U.S. Pat. No. 3,332,950 Blumberg et al
U.S. Pat. No. 3,254,088 Lowenstein et al
U.S. Pat. No. 4,451,470 Ganti The Ganti patent discusses the substitution at the 14 position with fluorine (the present invention is a 6-fluoro) but there is no phenolic compounds at column 1. The present invention does not have a teaching of a morphinan compound with the fluoro at the 14 position. Ganti's uses for the compound were for treating obesity, pain and narcotic addiction, whereas the present invtion's uses are for diagnostic imaging for opiate receptors.

EXAMPLES

Melting points were determined on a Fischer-Johns apparatus and were corrected. NMR spectra were recorded using a Varian 220 MHz spectrometer with Si(CH$_3$)$_4$ as the internal reference. Infrared spectra were recorded on a Beckman 4230 spectrometer. Silica gel GF plates for thin layer chromatography were purchased from Analtech, Inc., Newark, Del. Chemical ionization mass spectra (CIMS) were obtained on a Finnigan 1015D spectrometer with a Model 6000 data collection system and electron ionization mass spectra (EIMS) were obtained on a Hitachi-Perkin Elmer RMU-6E spectrometer (70 eV). Column chromatography was performed using 230–400 mesh EM silica gel. Mass spectra and elemental analysis were obtained from the Section on Analytical Services and Instrumentation, NIADDK.

EXAMPLE 1

4,5α-Epoxy-17-methyl-3,6α,14-trihydroxymorphinan (14-hydroxydihydromorphine, 5)

A solution of 1. 0 g (3.2 mmol) of 6α,14-dihydroxy-4,5α-epoxy-3-methoxy-17-methyl-morphinan (14-hydroxydihydrocodeine, 2) in CHCl$_3$ (30 mL) was stirred at 20° C. with BBr$_3$ (1.8 mL, 6 eq) for 30 min. The resulting white suspension was cautiously treated with MeOH until no further reaction occurred, then evaporated to a foam and partitioned between aqueous Na$_2$CO$_3$ (10 mL) and CHCl$_3$ (3×30 mL). Evaporation of CHCl$_3$ and crystallization from MeOH/ether gave 5 as white crystals (650 mg 67%), mp 250°–252° C.

EXAMPLE 2

3-Acetoxy-4,5α-epoxy-14-hydroxy-17-methyl-6α-trifluoromethanesulfonyloxymorphinan (8)

A solution of 2.0 g (5.8 mmol) of 3-acetoxy-6α,14-dihydroxy-4,5α-epoxy-17-methylmorphinan (mp 125.0°–126.5° C., previously reported as gum) in CHCl$_3$ (30 mL) with pyridine (4 mL) was stirred at 20° C. while two additions of 970 μL (1.63 g, 5.8 mmol) if trifluoromethanesulfonic anhydride were made. After 20 min, TLC (CHCl$_3$:MeOH:NH$_4$OH;90:10:1) indicated a single product spot (Rf=0.57) with no starting material (Rf=0.43). The mixture was partitioned between aqueous NaHCO$_3$ (50 mL) and CHCl$_3$ (2×30 mL), dried (Na$_2$SO$_4$) and evaporated to a red oil. Silica gel flash chromatography (CH$_2$Cl$_2$:MeOH 10:1) provided 8 as a yellow oil homogeneous on TLC (2.0 g, 72%); CIMS (NH$_3$) m/e 378 (M+1); NMR (CDCl$_3$): 1.43–1.77 (m, 4H), 1.93–2.10 (m, 1H), 2.16–2 32(m, 3H), 2.29 (s, 3H), 2.35 (s, 3H), 2.43 (d, 1H, J=7 Hz) 2.59 (dd, 1H, J=6 Hz and 18 Hz), 2.80 (d, 1H, J=6 Hz), 3.18 (d, 1H, J=18 Hz), 4.74 (d, 1H, J=4 Hz), 5.41 (quintet, 1H, J=4 Hz), 6.67 (d, 1H, J=8 Hz), 6.86 (d, 1H, J=8 Hz).

EXAMPLE 3

3,14-Dihydroxy-4,5α-epoxy-6β-fluoro-17-methylmorphinan hydrochloride (FOXY.HCl, 10.HCl)

A solution of triflate 8 (1.0 g, 2.1 mmol) in acetonitrile (30 mL) was stirred at reflux with KF (880 mg, 15.2 mmol) and 18-crown-6 ether (1.1 g, 4.2 mmol). The reaction was complete at 2 min by TLC. It was evaporated and purified by silica gel flash chromatography (CH$_2$Cl$_2$:MeOH:NH$_4$OH 100:5:1) yielding the 3-OAc derivative of FOXY 9 as a syrup. This was dissolved in MeOH (10 mL) and stirred at 80° C. for 30 min with concentrated NH$_4$OH (500 μL). The solvent was evaporated to yield crude product as a crystalline solid which was acidified with methanolic HCl and crystallized from 2-propanol/isopropyl ether, yielding 10.HCl as a white crystalline solid (440 mg, 62%): mp 196°–200° C.: CIMS (NH$_3$) m/e 306 (M+1); NMR (CDCl$_3$): 1.20–1.50 (m, 3H), 1.57–1.70 (m, 1H), 1.75–1.95 (m, 1H), 2.05–2.30 (m, 3H), 2.36 (s, 3H), 2.53 (dd, 1H, J=6 Hz and 18 Hz), 2.78 (d, 1H, J=6 Hz), 2.66 (d, 1H, J=18 Hz), 4.34 (doublet of quintets, 1H, J=6 Hz and 49 Hz), 4.61 (dd, 1H, J=6 Hz and 21 Hz), 6.57 (d, 1H, J=8 Hz), 6.70 (d, 1H, J=8 Hz). Anal. Calcd. for C$_{17}$H$_2$O$_3$F.HCl.2.5 H$_2$O: C, 52.78; H, 6.77; N, 3.62. Found: C, 52.79; H, 6.42, N, 3.31.

EXAMPLE 4

3-Acetoxy-17-cyclopropylmethyl-4,5α-epoxy-6α-hydroxymorphinan oxalate (14 oxalate)

Naltrexone.HCl (11.HCl) (20 g, 53 mmol) was dissolved in H$_2$O (200 mL) by warming, then made alkaline by addition of NH$_4$OH (30 mL) and extracted with CHCl$_3$ (3×100 mL). Evaporation of the CHCl$_3$ extract gave naltrexone base as a white solid in quantitative yield. This was dissolved in THF (200 mL) and cooled on ice while NaBH$_4$ (1.0 g, 26 mmol) was added. After 1 h excess hydride was destroyed by stirring for 30 min with dilute HCl (5 mL). Evaporation of the solvent left a foam which was partitioned between dilute NH$_4$OH (20 mL) and CHCl$_3$ (2×150 mL), washed with dilute NH$_4$OH (100 mL) and evaporated to a white foam containing predominantly 6 —OH isomer 12 with a little 6β-OH isomer 13. The foam was mixed with H$_2$O (400 mL) containing NaHCO$_3$ (50 g), then acetic anhydride was added (30 mL) and the mixture stirred at 20° C. for 40 min. The resulting clear solution was extracted with CHCl$_3$ (3×100 mL), evaporated to a syrup and purified by silica gel flash chromatography (CH2Cl$_2$:MeOH:NH$_4$OH; 100:5:1) to yield pure 6α-OH 14 as a syrup. Crystallization of the oxalate salt (1 mol eq of oxalic acid) from acetic MeOH gave 14 oxalate as a white salt (9.4 g, 37% yield): mp 184°–187° C. (gas); NMR (CDCl$_3$;δ4.6 (d, 5β-H, J$_{5β-6β}$=5.0 Hz); (d, 5β-$_H$, J$_{5β-6β}$=5.2 Hz). Anal. Calcd. for C$_{22}$H$_{27}$NO$_5$.C$_2$H$_2$O$_4$.

1.5 H$_2$O: C, 57.36; H, 6.42; H, 2.79. Found: C, 57.45; H, 6.21; N, 2.86.

EXAMPLE 5

3-Acetoxy-17-cyclopropylmethyl-4,5α-epoxy-6α-trifluoromethanesulfonyloxymorphinan (16)

Oxalate salt 14 (4.8 g, 10 mmol) was partitioned between aqueous NaHCO$_3$ (50 mL) and CHCl$_3$ (2×100 mL). Evaporation of the CHCl$_3$ extracts gave free amine 14 as a colorless syrup in quantitative yield. This was taken up in CHCl$_3$ (30 mL) to which was added pyridine (4 mL), then trifluoromethanesulfonic anhydride (2×1.7 mL, 20 mmol total). After 10 min the reaction mix was diluted with CHCl$_3$ (100 mL) washed with aqueous NaHCO$_3$, dried (Na$_2$SO$_4$) and evaporated to a red oil. Silica gel flash chromatography (CH$_2$Cl$_2$:MeOH:NH$_4$OH 100:5:1) gave product 16 as a yellow syrup, (5.0 g, 97%): CIMS (NH$_3$) m/e 518 (M+1); NMR (CDCl$_3$): 0.14 (d, 1H, J=5 Hz), 0.56 (d, 1H, J=8 Hz), 0.68–0.91 (m, 1H), 1.43–1.77 (m, 4H), 1.93–2.10 (m, 1H), 2.24–2.39 (m, 3H), 2.17 (s, 3H), 2.30 (s, 3H), 2.70–3.02 (m, 2H), 3.04–3.60 (m, 2H), 4.76 (d, 1H, J=4 Hz), 5.34–5.45 (m, 1H), 6.66 (d, 1H, J=8 Hz), 6.86 (d, 1H, J=8 Hz).

EXAMPLE 6

17-Cyclopropylmethyl-3,14-dihydroxy-4,5α-epoxy-6β-fluoromorphinan hydrochloride (CYCLOFOXY.HCl,18.HCl)

Triflate 16 (3.26 g, 6.3 mmol) in acetonitrile (100 mL) was stirred at reflux with KF (3.9 g, 68 mmol) and 18-crown-6 ether (5.1 g, 19.3 mmol). After 1 h the reaction was removed, evaporated to a gum and purified by silica gel flash chromatography (CH$_2$Cl$_2$:NH$_{40}$ OH 100:1) to yield 3-OAc 17 as a foam (1.0 g). This was dissolved in MeOH (50 mL) and stirred with NH$_4$OH (1 mL) for 1.5 h. The reaction mixture was then evaporated, acidified with methanolic HCl and crystallized from 2-propanol: isopropyl ether to yield 18.HCl as white crystals (890 mg, 37% yield): mp 206°–210° C.; EIMS m/e 345 (M+); NMR (CDCl$_3$): 0.11 (d, 2H, J=5 Hz), 0.52 (d, 2H, J=8 Hz), 0.74–0.92 (m, 1H), 1.23–1.52 (m, 3H), 1.59–1.74 (m, 1H), 1.77–1.93 (m, 1H), 2.05–2.30 (m, 2H), 2.36 (d, 2H, J=7 Hz), 2.48–2.68 (m, 2H), 3.00 (d, 1H, J=18 Hz), 3.56 (d, 1H, J=6 Hz), 4.34 (doublet of quintets, 1H, J=6 Hz and 48 Hz), 4.61 (dd, 1H, J=6 Hz and 21 Hz), 6.55 (d, 1H, J=8 Hz), 6.70 (d, 1H, J=8 Hz). Anal. Calcd. for C$_{20}$ OH$_{25}$ClFNO$_3$: C, 62.91; H, 6.60; N, 3.67. Found: C, 62.55; H, 6.87; N, 3.28.

EXAMPLE 7

3,14-Dihydroxy-4,5α-epoxy-6β-fluoro-17-methylmorphinan-1,2-$^3$H ($^3$H-FOXY, 20)

To a solution of FOXY.HCl, (18HCl) (240 mg, 0.79 mmol) in AcOH (5 mL) was added 5 drops of 48% aqueous HBr and bromine vapor was passed over the stirred solution. After 1.5 h solvent was evaporated and the residue partitioned between aqueous NaHCO$_3$ (5 mL) and CHCl$_3$ (10 mL). Evaporation of the CHCl$_3$ extract gave a foam which was purified by siica gel flash chromatography (CH$_2$Cl$_2$: MeOH:NH$_4$OH;90:5:0.5) to yield 19 as a syrup. Acidification with methanolic HCl gave 19.HCl as a white amorphous powder (155 mg, 39%): CIMS (NH$_3$) 460, 461, 463 (isotopic distribution for M+1); NMR (CDCl$_3$, free base): 1.20–1.50 (m, 3H), 1.57–1.70 (m, 1H), 1.75–1.95 (m, 1H), 2.05–2.30 (m, 3H), 2.37 (s, 3H), 2.34–2.52 (m, 1H), 2.85 (d, 1H, J=6 Hz), 2.66 (d, 1H, J=18 Hz), 4.34 (doublet of quintets, 1H, J=6 Hz and 49 Hz), 4.61 (dd, 1H, J=6 Hz and 21 Hz).

A solution 19.HCl (10 mg) in MeOH (2 mL) was stirred with 10% Pd C (15 mg) under an atmosphere of tritium gas (25 Ci). (Tritiation was performed at the New England Nuclear Corp., 549 Albany St., Boston, Mass., 62118.) After 24 h the mixture was filtered, labile tritium removed in vacuo and the residue (311 mCi) taken up in MeOH (2 mL). A 30 mCi aliquot was applied to a 2.5 cm×9 cm aluminum backed EM silica gel 60 TLC plate (200μ), and developed (CHCl$_3$:MeOH:-NH$_4$OH: 100:3:3). The plate was cut into 7×1 cm bands which were each eluted with MeOH (2 mL) and aliquots subjected to liquid scintillation spectrophotometry. Bands 5 and 6, containing 48% of the total eluted activity, were pooled and rechromatographed in an identical manner, yielding $^3$H-FOXY 20 (2 mCi). When an aliquot of 20 was cochromatographed with authentic FOXY (10) (TLC, solvent system as above), 97% of the total radioactivity ran with 10 (visualized with I$_2$) indicating 97% radiochemical purity. The UV spectrum of 20 was identical with authentic 10, and specific activity of 20 was calculated as 16 Ci/mmol based upon its uv absorption at 285 nm.

EXAMPLE 8

The utility by which the opiate receptors were visualized in the living baboon was as follows. The baboon was put under general anesthesia and the vital signs stabilized and then he was injected i.v. with acetylcyclofoxy, which is metabolically converted to Cyclofoxy within minutes in the baboon. Then in the baboon's brain, whose head is in the PETT scanner, the receptors are visualized, detected by the PETT scanner and through the use of computers is converted to an image on the screen. By this method the basal ganglia in the baboon's brain, which are known to contain opiate receptors, were clearly visible and with lower slices the thalamus, also known to contain opiate receptors from many different studies, were also visualized. The receptor occupancy is quantitated by the computer to give the number of molecules of Cyclofoxy which are bound to the opiate receptors in the baboon's brain. The ability to be able to visualize opiate receptors by a non-invasive technique such as this has many implications in the study of the structure and function of opiate receptors and distribution in the various areas of the brain, and the function of these receptors in the overall modulation of the central nervous system in primates. The present results now permit study of opiate receptors in normal and diseased states of the central nervous system and in other cells with opiates receptors such as in small cell lung cancer. Opiate receptors in the central nervous system are involved in many aspects of the regulation of pain, pleasure, and mood in animals and man and the ability to be able to study these effects as a function of the external stimuli will provide much information on the function of the central nervous sytem in animals including man.

DOSAGE

The amount of $^{18}$F Foxy and $^{18}$F Cyclofoxy and their $^3$H tritiated derivatives is utilized in an amount sufficient for coverage of the opioid receptor system and visualization of highly specific mu opiate receptor ligands.

In the specification and claims the designation for the labeled $^{18}$F derivatives, is shown as a prime number, as in Compounds 9', 10', 17', and 18'. Furthermore, the non-labeled derivatives are designated without a special label, as in Compounds 17 and 18.

We claim:

1. A compound according to the following formula:

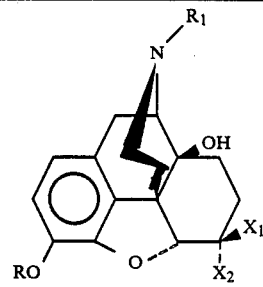

| | R | R$_1$ | X$_1$ | X$_2$ |
|---|---|---|---|---|
| 9' | Ac | Me | $^{18}$F | H |
| 10' | H | Me | $^{18}$F | H |
| 17' | Ac | CPM | $^{18}$F | H |
| 18' | H | CPM | $^{18}$F | H | where CPM is cyclopropylmethyl, and Ac=C$_2$–C$_6$ acyl.

2. A compound according to the following formula:

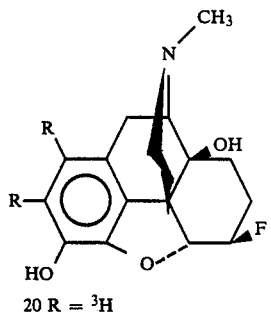

20 R = $^3$H

3. A compound selected from the group consisting of [$^{18}$F] 3,14-dihydroxy-4,5α-epoxy-6α-epoxy-6β-fluoro-17-methyl-morphinan ($^{18}$F-FOXY 10') or 3,14-dihydroxy-4,5α-epoxy-6β-fluoro-17-methylmorphinan-1b 1,2-$^3$H ($^3$H-FOXY 20).

4. [$^{18}$F]17-cyclopropylmethyl-3,14-dihydroxy-4,5α-epoxy-6β-fluoromorphinan ($^{18}$F-CYCLOFOXY 18').

* * * * *